United States Patent [19]

Ely

[11] Patent Number: 5,196,448

[45] Date of Patent: Mar. 23, 1993

[54] ANTIINFLAMMATORY COMPOSITIONS AND METHOD OF USE

[75] Inventor: Parry H. Ely, Nevada City, Calif.

[73] Assignee: Stiefel Laboratories, Inc., Coral Gables, Fla.

[21] Appl. No.: 643,219

[22] Filed: Jan. 22, 1991

[51] Int. Cl.$^5$ ............... A61K 31/335; A61K 31/445; A61K 31/535

[52] U.S. Cl. ..................... 514/452; 514/316; 514/321; 514/232.5; 514/233.8

[58] Field of Search ............ 514/452, 316, 321, 232.5, 514/233.8

[56] References Cited

U.S. PATENT DOCUMENTS 4,895,839  1/1990  Bombardelli ..................... 514/78

FOREIGN PATENT DOCUMENTS 180505   10/1985  France .
2597337  1/1987   France .
2609630  1/1987   France .

OTHER PUBLICATIONS

Merck Index, 10th Ed. (1983), Monograph No. 8372.
Ely, "Dermatologic Therapies You've Probably Never Heard Of", *Dermatologic Clinics*, vol. 7 (1989) pp. 19, 25–28.
Bonne et al., "Screening Tests of Free Ridical Scavengers for Preventing Sun-Accelerated Cutaneous Ageing", Intl. J. Cosmetic Sci., vol. 10 (1988) pp. 247–252.
Weber, et al., "The Liver-A Therapeutic Target in Cases of Dermatosis", *Medwelt*, vol. 34 (1983) pp. 50–55.
"Chemistry of Silymarin and Water-Soluble Derivatives", *Symposium on the Pharmacodynamics of Silymarin* (1976) pp. 7–12.
Stedman's Medical Dictionary, 24 Ed., Williams & Wilkins, Baltimore, Md., p. 1509.

*Primary Examiner*—Jerome D. Goldberg
*Attorney, Agent, or Firm*—Mathews, Woodbridge & Collins

[57] ABSTRACT

Esters of silybin with dicarboxylic acids, and the salts thereof, are antiinflammatory agents. A typical example is the disodium salt of the bis-(hemisuccinate).

5 Claims, No Drawings

ANTIINFLAMMATORY COMPOSITIONS AND METHOD OF USE

The present invention pertains to topical preparation for the treatment of inflammatory dermatoses and to a method of treating inflammatory dermatoses.

In particular, the invention relates to compositions comprising (a) an effective amount of (i) a dicarboxylic acid of the formula:

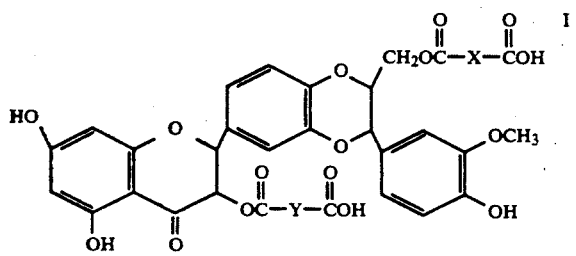

in which each of X and Y, independently of the other, is alkylene of from 1 to 6 carbon atoms or phenylene, or (ii) a pharmaceutically acceptable mono or dicationic alkali metal, alkaline earth metal, ammonia, or organic amine salt thereof.

The invention also relates to the method of treating inflammatory dermatoses by topically applying to the loci of the dermatosis an effective amount of a dicarboxylic acid of Formula I or a pharmaceutically acceptable mono or dicationic alkali metal, alkaline earth metal, ammonia, or organic amine salt thereof.

In the compounds of Formula I, each of X any Y can be a straight or branched alkylene chain of 1 to 6 carbon atoms, such as methylene, ethylene, ethylidene, trimethylene, propane-1,2-diyl, propylidene, tetramethylene, 2,2-dimethylpropane-1,3-diyl, pentamethylene, hexamethylene, and the like, or phenylene such as 1,2-phenylene, 1,3-phenylene, and 1,4-phenylene. X and Y can be different from one other but generally are the same. Preferably each of X and Y is alkylene of 1 to 4 carbon atoms and most preferably within this subclass, each of X and Y is $-CH_2CH_2-$.

The composition and method of this invention can employ the foregoing diacids or alternatively can employ a pharmaceutically acceptable mono or dicationic alkali metal, alkaline earth metal, ammonia, or organic amine salt as, for example, a salt having one mono or divalent cation or two monovalent cations, as for example sodium, potassium, magnesium, calcium, protonated amines such as those derived from ethylamine, triethylamine, ethanolamine, diethylamino-ethanol, ethylenediamine, piperidine, morpholine, 2-piperidinoethanol, benzylamine, procaine and the like. Particularly preferred and the disodium salts of the dicarboxylic acids of Formula I.

The foregoing dicarboxylic acids of Formula I are in some instances known but in any event can be prepared by conventional esterification techniques. Thus the known 2-[2,3-dihydro-3-(4-hydroxy-3-methoxyphenyl)-2-hydroxymethyl-1,4-benzodioxin-6-yl]-2,3-dihydro-3,5,7-trihydroxy-4H-1-benzopyran-4-one, also known as silybin or silymarin I (see Hänsel et al., Chem. Commun., 1972. 195) can be esterified with alkanedicarboxylic acids such as malonic, succinic, glutaric, adipic, phthalic, isophthalic, or terephthalic acid, or with reactive derivatives thereof such as acid halides or anhydrides. As noted, some derivatives such as the bis-(hemisuccinate) are commercially available. Formation of the salts can be readily accomplished by simple titration of the diacid with an appropriate base such as sodium hydroxide.

The treatment of inflammatory dermatoses preferably is carried out employing a compositions in which an effective amount of one or more compounds of Formula I or a salt thereof is admixed with a topically acceptable pharmaceutical carrier.

In a further aspect, the invention relates to compositions including an effective amount of a topically acceptable steroidal anti-inflammatory agent. For example, suitable steroids include betamethasone dipropionate or valerate, clobetasol propionate, clocortolone pivalate, desonide, desoximetasone, dexamethasone, fluocinolone acetonide, fluocinonide, halcinonide, hydrocortisone, methylprednisolone acetate, triamcinolone acetonide, or anti-inflammatory derivatives thereof. Suitable derivatives include esters.

Hydrophilic or solvent formulations utilizing various physiologically acceptable liquids can be employed in major amounts, normally ranging from about 75 to 99.95 weight percent. Acceptable solvents include ethanol, propylene glycol, and water. Surfactants can be added, either individually or in combination, and normally will be present in an amount from about 0.1 to a total of 5 weight percent of the composition. The surfactants can be non-ionic, anionic or cationic, including polyethylene glycol, their esters and ethers, alkylbenzene sulfonates, soaps, and the like. Physiologically acceptable thickening agents also can be added, normally in amounts of from about 0.1 to 2 weight percent, when a gel is desired. Antioixidants can be added, such as BHT and BHA, normally in minor amounts, generally from about 0.01 to 0.5 weight percent. Bacteriostatic and bactericidal agents also can be added in minor amounts. Emollients such as glycerine also can be added in amounts ranging from about 5 to 15 weight percent. Also, buffers can be added or mineral bases to provide the desired pH. Such formulations can be applied as lotions, solutions, or aerosol sprays.

Lipophilic formulations, such as anhydrous creams and ointments, generally will have a base derived from fatty alcohols, and polyethylene glycols. Additional additives include alcohols, non-ionic surfactants, and antioxidants. For ointments, the base normally will be an oil or mixture of oil and wax, e.g., petrolatum. Also, an antioxidant normally will be included in minor amounts.

Because the compositions are applied topically and the effective dosage can be controlled by the total composition applied, the percentage of active ingredient in the composition can vary widely. Convenient concentrations range from 0.5% to 20%. The compositions are applied as needed in the treatment of such conditions as acne, atopic dermatitis, contact dermatitis, poison ivy, and the like.

The following examples will serve to further typify the nature of this invention.

EXAMPLE 1

Ointment

An ointment is prepared by combining 20.0% (w/w) of silymarin bis-(hemisuccinate) and 80.0% (w/w) of petrolatum. The mixture is passed through a roller mill until a uniform consistency is obtained. A small amount of the ointment is applied to the inflamed area.

EXAMPLE 2

Solution

Silymarin bis-(hemisuccinate), 10.0% (w/w), is combined with 30.0% (w/w) of glycerin and 60.0% (w/w) of ethanol and thoroughly mixed to form a solution suitable for topical application.

EXAMPLE 3

Aerosol Spray

A solution is prepared from the following components:

| Ingredient | Amount (w/w) |
| --- | --- |
| Silymarin bis-(hemisuccinate) | 1.00 |
| Propylene Glycol | 5.00 |
| Polysorbate 80 | 1.00 |
| Ethanol | 78.00 |
| Purified Water | 15.00 |

The solution is placed in a conventional aerosol container, a valve mechanism is attached, and the container is charged with nitrogen to 100 psig.

EXAMPLE 4

Lotion

| | |
| --- | --- |
| Disodium silymarin bis-(hemisuccinate) | 1.00 |
| Glycerin | 3.00 |
| Mineral Oil | 3.00 |
| Stearic Acid | 2.00 |
| Glycol stearate | 1.30 |
| Cetyl Acetate/acetylated lanolin alcohol | 1.00 |
| Triethanolamine | 1.00 |
| Cetyl alcohol | 0.75 |
| Methylparaben | 0.50 |
| Propylene Glycol | 0.50 |
| Carbomer 934R | 0.30 |
| Dimethicone | 0.30 |
| Magnesium Aluminum Silicate | 0.25 |
| Disodium Ethylenediaminetetraacetic Acid | 0.10 |
| Propylparaben | 0.10 |
| Purified Water | 84.90 |

The foregoing components are thoroughly blended to produce a 1% lotion.

EXAMPLE 5

Ointment

An ointment is prepared by combining 20.000% (w/w) of silymarin bis-(hemisuccinate), 0.025% (w/w) of fluocinolone acetonide, and 79.975% (w/w) of petrolatum. The mixture is passed through a roller mill until a uniform consistency is obtained. A small amount of the ointment is applied to the inflamed area.

What is claimed is:

1. The method of treating inflammatory dermatoses which comprises topically applying to the loci of the dermatosis an effective amount of a preparation comprising (a) from 0.5% to 20% by weight of (i) a dicarboxylic acid of the formula:

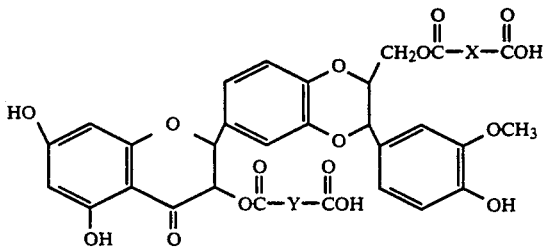

in which each of X and Y, independently of the other, is alkylene of from 1 to 6 carbon atoms or phenylene, or (ii) a pharmaceutically acceptable salt thereof having one or two cations in which the cation is selected from the group consisting of the cationic form of alkali metal, alkaline earth metal, ammonia, ethylamine, triethylamine, ethanolamine, diethylaminoethanol, ethylenediamine, piperidine, morpholine, 2-piperidinoethanol, benzylamine and procaine; and (b) a topically acceptable pharmaceutical carrier therefor.

2. The method according to claim 1 wherein each of X and Y is alkylene of 1 to 4 carbon atoms.

3. The method according to claim 2 wherein each of X and Y is —CH$_2$CH$_2$—.

4. The method according to claim 1 wherein said dicarboxylic acid is the disodium salt.

5. The method according to claim 1 wherein said dicarboxylic acid is applied in a lotion base.

* * * * *